(12) United States Patent
Negishi

(10) Patent No.: US 8,298,008 B2
(45) Date of Patent: Oct. 30, 2012

(54) MOUNTING ASSEMBLY AND CABLE ASSEMBLY

(75) Inventor: Nau Negishi, Yokohama (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/402,156

(22) Filed: Feb. 22, 2012

(65) Prior Publication Data

US 2012/0149238 A1 Jun. 14, 2012

Related U.S. Application Data

(63) Continuation of application No. PCT/JP2010/063466, filed on Aug. 9, 2010.

(30) Foreign Application Priority Data

Sep. 17, 2009 (JP) .................................. 2009-215557

(51) Int. Cl.
*H01R 9/05* (2006.01)
(52) U.S. Cl. ........................................................ 439/579
(58) Field of Classification Search .................. 439/579, 439/942; 174/113 R
See application file for complete search history.

(56) References Cited

U.S. PATENT DOCUMENTS 6,162,086 A * 12/2000 Kuo ................................ 439/497
7,413,474 B2 * 8/2008 Liu et al. ......................... 439/579
7,750,240 B2 * 7/2010 Jiang et al. ................. 174/102 R
2009/0120662 A1 5/2009 Tanaka

FOREIGN PATENT DOCUMENTS

| JP | 2001-035567 | 2/2001 |
| JP | 3863583 | 10/2006 |
| JP | 2009-123459 | 6/2009 |

OTHER PUBLICATIONS

English Abstract of Japanese Patent Publication No. 09-090237, dated Apr. 4, 1997.
International Search Report dated Sep. 7, 2010 issued in PCT/JP2010/063466.

* cited by examiner

*Primary Examiner* — Tho D Ta
(74) *Attorney, Agent, or Firm* — Scully, Scott, Murphy & Presser, PC

(57) ABSTRACT

In a cable assembly including signal lines formed by core wires, inner insulating bodies, outer conducting bodies, and outer insulating bodies, respectively, the signal lines in the cable assembly are formed in a manner of exposing respective outer conducting bodies from respective outer insulating bodies in an area at least including respective distal edges, an array block fixes the signal lines in a state where side surfaces of neighboring outer conducting bodies among the exposed outer conducting bodies are in contact, and a core wire electrode part and an outer conducting body electrode part which is connected to a part of edge faces of the plurality of outer conducting bodies fixed in the state where the side surfaces are in contact are formed on a circuit board to be connected to the cable assembly.

6 Claims, 13 Drawing Sheets

MOUNTING ASSEMBLY AND CABLE ASSEMBLY

CROSS-REFERENCE TO RELATED APPLICATION

This application is a continuation of International Application No. PCT/JP2010/063466, designating the United States and filed on Aug. 9, 2010 which claims the benefit of priority from Japanese Patent Application No. 2009-215557, filed on Sep. 17, 2009, and the entire contents of the International application and the Japanese Application are incorporated herein by reference.

BACKGROUND OF THE INVENTION

1. Field of the Invention

The present invention relates to a cable assembly and a mounting assembly provided with a cable assembly and a substrate connected to the cable assembly.

2. Description of the Related Art

In recent years, an endoscope for medical and industrial purposes have been widely used, and especially a medical endoscope enables an observation of a lesion site when an insertion unit is deeply inserted to an inside of a body and further enables an examination and a medical treatment in the inside of the body by using a treatment tool together depending on a necessity. As such an endoscope, there is an endoscope provided with an imaging device in which an imaging element such as a CCD is embedded at a distal end of the insertion unit. In the endoscope, an image captured by the imaging element is displayed on a monitor to observe the inside of the body by a process in which an electrical signal obtained after a conversion of the image captured by the imaging element is transmitted to a signal processor via a signal line and undergoes a process in the signal processor. The imaging element and the signal processor in the endoscope are connected for the purpose of transmitting an image signal and a clock signal, supplying a driving power to the imaging element, and the like by a cable assembly which bundles a plurality of signal lines.

Conventionally, a method of using, as a hard part constituting a connection terminal part of the cable assembly, an array block provided with a plurality of fixation holes to which respective signal lines can be inserted and fixing the respective signal lines at predetermined respective arrangement positions has been proposed, and a length of the hard part is shortened to downsize the insertion unit of the endoscope. More detailed information can be obtained from Japanese Patent Publication No. 3863583.

In this case, a connection surface is formed by grinding the signal lines in a manner of exposing respective edge faces of the signal lines which are fixedly arranged in the array block in the cable assembly. The cable assembly and the imaging element are then connected collectively by compressively bonding on the connection surface a circuit board to be electrically connected to the imaging element via an anisotropic conductive adhesive film or an anisotropic conductive adhesive paste.

SUMMARY OF THE INVENTION

According to an aspect of the present invention, in a mounting assembly provided with: a cable assembly including a plurality of signal lines each of which is formed by a core wire, an inner insulating body which covers the core wire, an outer conducting body which covers the inner insulating body, and an outer insulating body which covers the outer conducting body; and a substrate to be connected to the cable assembly, the cable assembly includes a fixation member that fixes the plurality of signal lines in a predetermined array state, the signal lines are formed in a manner of exposing respective outer conducting bodies from respective outer insulating bodies in an area at least including respective distal edges, the fixation member fixes the signal lines in a state where side surfaces of neighboring outer conducting bodies among the exposed outer conducting bodies are in contact and in a manner of exposing respective edge faces of the plurality of outer conducting bodies and respective edge faces of the plurality of core wires, and the substrate includes an electrode part formation surface which is a surface on which a plurality of core wire electrode parts and an outer conducting body electrode part are formed and faces an edge face exposure surface of the fixation member, the plurality of core wire electrode parts being connected to the respective edge faces of the core wires in the plurality of signal lines and the outer conducting body electrode part being connected to a part of the edge faces of the plurality of outer conducting bodies fixed in the state where the side surfaces are in contact.

According to another aspect of the present invention, a cable assembly including a plurality of signal lines each of which is formed by a core wire, an inner insulating body which covers the core wire, an outer conducting body which covers the inner insulating body, and an outer insulating body which covers the outer conducting body, includes a fixation member that fixes the plurality of signal lines in a predetermined array state, wherein the signal lines are formed in a manner of exposing respective outer conducting bodies from respective outer insulating bodies in an area at least including respective distal edges, and the fixation member fixes the signal lines in a state where side surfaces of neighboring outer conducting bodies among the exposed outer conducting bodies are in contact.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENT

An exemplary embodiment of a mounting assembly and a cable assembly according to the present invention will be explained below by taking a mounting assembly and a cable assembly used for a medical endoscopic device provided with an imaging device at a distal end of an insertion unit as an example. It should be noted that the present invention is not limited to the embodiment. The same part is assigned with the same reference symbol in the description of the drawings. It should also be noted that the accompanying drawings are merely schematic and a relation between a thickness and a width of each member, a ratio of each member, and the like may be different from the reality. The dimensional relations and the ratio may be different from one drawing to another.

Embodiment

Figure 1:
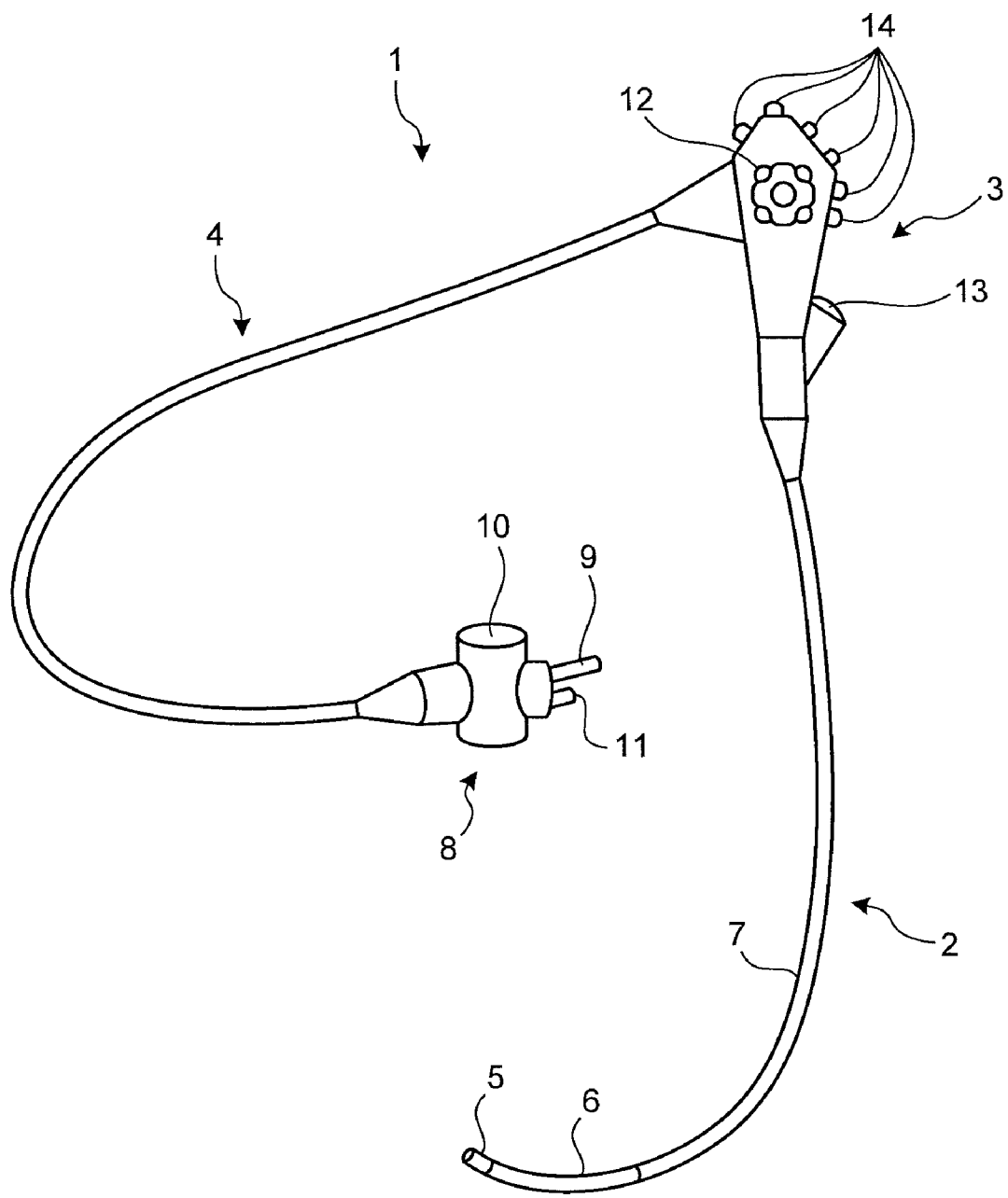
FIG. 1 is a schematic view of a configuration of an endoscopic device according to an embodiment.

First, an endoscopic device according to an embodiment will be explained. FIG. 1 is a schematic view of a configuration of an endoscopic device according to the embodiment. As shown in FIG. 1, an endoscopic device 1 according to the embodiment is provided with an elongated insertion unit 2, an operation unit 3 that locates at a base end side of the insertion unit 2 and is grasped by an operator of the endoscopic device, and a flexible universal cord 4 that extends from a side part of the operation unit 3. The universal cord 4 houses therein a light guiding cable, an electrical system cable, and the like.

The insertion unit 2 is provided with a distal end part 5 incorporating an imaging element such as a CCD, a bend part 6 that is constituted by a plurality of bend pieces and can freely bend, and a flexible tube part 7 that is long, flexible, and provided at a base end side of the bend part 6.

A connector part 8 is provided at an end part at a side of the extension of the universal cord 4. The connector part 8 is provided with a light guiding connector 9 which is detachably connected to a light source, an electrical contact part 10 that allows transmitting an electrical signal, obtained via a photoelectric conversion by the CCD and the like, of a subject image to a signal processor or a controller, an air feeding cap 11 that allows feeding air to a nozzle of the distal end part 5, and the like. The light source is a device incorporating a halogen lamp and the like and supplies a light from the halogen lamp to the endoscopic device 1 connected via the light guiding connector 9 as an illumination light. The signal processor and the controller serve as a device that supplies power to the imaging element and receives an electrical signal obtained via the photoelectric conversion from the imaging element, processes the electric signal captured by the imaging element, makes a connected displaying device display an image, and outputs a driving signal by which a control and a driving of a gain adjustment and the like of the imaging element are performed.

The operation unit 3 is provided with a bend knob 12 that enables the bend part 6 to bend to a vertical direction and a horizontal direction, a treatment tool inserting part 13 from which treatment tools such as a biopsy forceps and a laser probe are inserted to an inside of a body cavity, and a plurality of switches 14 by which the signal processor, the controller, and peripheral equipment such as an air feeding device, a water feeding device, and a gas feeding device are operated. The endoscopic device 1 in which a treatment tool is inserted to a treatment tool inserting opening allows a distal end treatment part of the treatment tool to project via a treatment tool inserting channel internally provided. The endoscopic device 1 performs, for example, a biopsy in which affected tissues are removed by a biopsy forceps, and the like.

Figure 2:
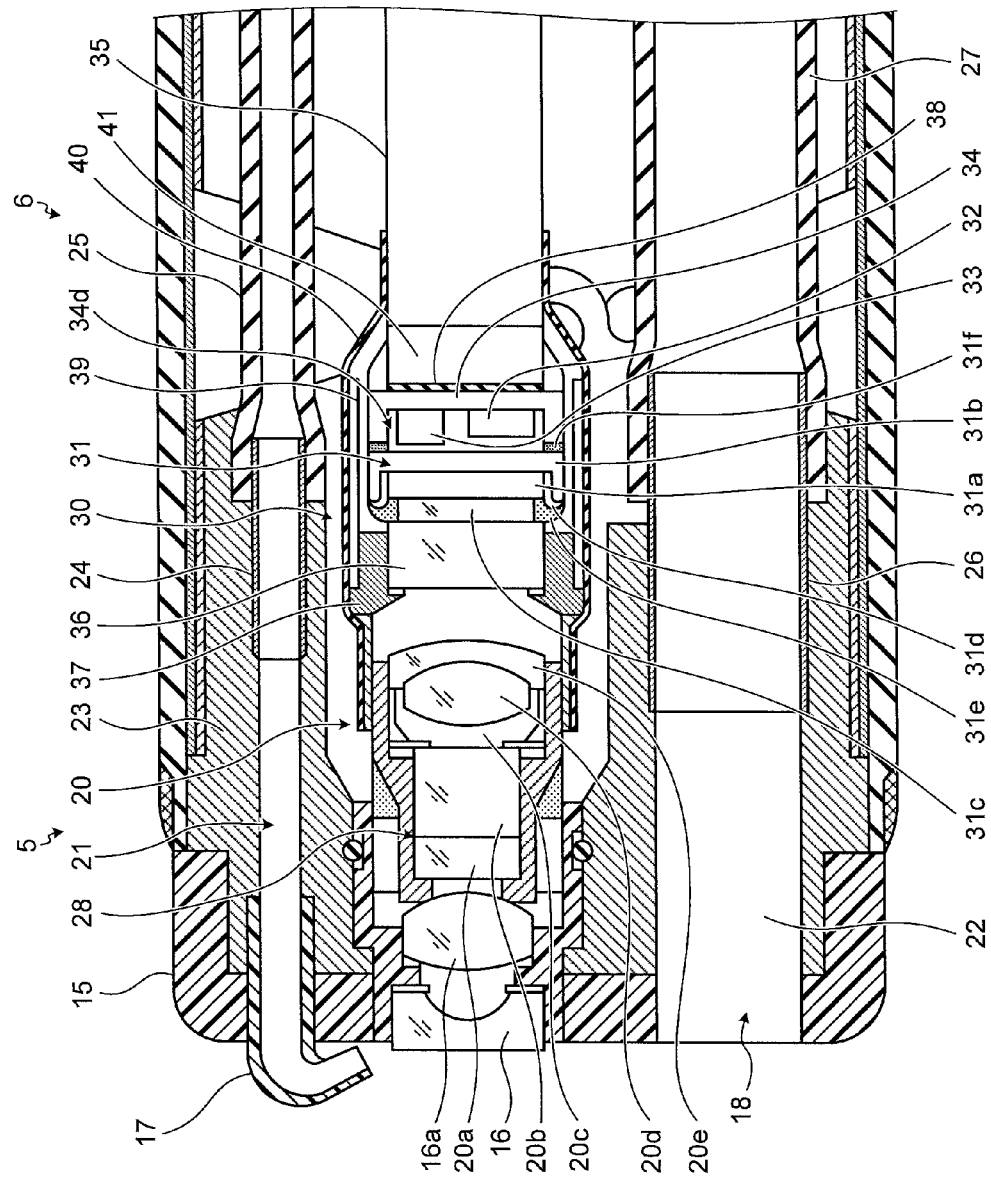
FIG. 2 is a cross sectional view for explaining an internal structure of a distal end part of the endoscopic device shown in FIG. 1.

Next, a structure of the distal end part of the endoscopic device 1 will be explained. FIG. 2 is a cross sectional view for explaining an internal structure of the distal end part 5 of the endoscopic device 1 shown in FIG. 1. As shown in FIG. 2, the distal end part is externally fitted with a distal end cover 15 in the distal end part 5 locating at a distal end side of the insertion unit 2 of the endoscopic device 1. The distal end cover 15 is provided with an observation window 16, a not-shown illumination lens, a nozzle 17 for feeding air and water, and a forceps opening 18. An imaging device 20 that captures images in an inside of a body cavity via a plurality of lenses including a lens 16a is inserted and fitted to the observation window 16. A distal end block 23 in which an air/water feeding passage 21, a forceps insertion passage 22 respectively corresponding to the nozzle 17 and the forceps opening 18, and the like are provided is provided at a rearward of the observation window 16.

At a rear end part of the air/water feeding passage 21 in the distal end block 23, an air/water feeding pipe 24 is provided. An air/water feeding tube 25 is connected to the air/water feeding pipe 24. At a rear end part of the forceps insertion passage 22, a forceps insertion pipe 26 is provided. A forceps insertion tube 27 is connected to the forceps insertion pipe 26.

The imaging device 20 is provided with an objective optical unit 28 constituted by a plurality of optical lenses 20a to 20e, a CCD unit 30 arranged at a rearward of the objective optical unit 28, and the like. The CCD unit 30 is provided with a CCD 31 that receives a light incident on the objective optical unit 28, a circuit board 34 mounting an IC 32 that processes an image signal at the CCD 31 into an electrical signal and a chip capacitor 33, a cable assembly 35 that transmits the electrical signal to a signal processor as an external device. The cable assembly 35 is provided with a plurality of signal lines.

At a light reception surface side of the CCD 31, a cover glass 36 is provided. An inner circumferential part of a CCD retaining frame 37 is fitted in an outer circumferential part of the cover glass 36 and integrally fixed by an adhesive agent and the like. The CCD 31 is provided with a CCD chip 31a having an imaging unit, a package 31b, a filter 31c, a bonding wire 31d, a sealing resin 31e, an electrode 31f, and the like, for example.

The circuit board 34 includes an electrode part on both surfaces. The circuit board 34 includes a concave part 34d on which the IC 32 and the chip capacitor 33 are mounted at a side of the imaging device 20. The electrode provided at the side of the imaging device 20 of the circuit board 34 is connected to the electrode 31f of the CCD 31.

The electrode (not shown) provided at a side of the cable assembly 35 of the circuit board 34 is in contact with a distal end surface of the cable assembly 35 via an anisotropic conductive adhesive film (ACF) 38. A shield frame 39 is provided at a rear end part of the CCD retaining frame 37 in a manner of covering the CCD 31 and the circuit board 34. An outer circumferential part at the distal end side of the shield frame 39 and the CCD retaining frame 37 is covered by a heat shrinkable tube 40. The CCD unit 30 is from the distal end part of the CCD retaining frame 37 to the rear end of the cable assembly 35. A hard part of the imaging device 20 is from the distal end surface of the CCD retaining frame 37 to the rear end of the heat shrinkable tube 40. An array block (fixation member) 41 that has an insulation property and fixes the plurality of signal lines in the cable assembly 35 in a predetermined array state is attached to the distal end of the cable assembly 35.

Figure 3:
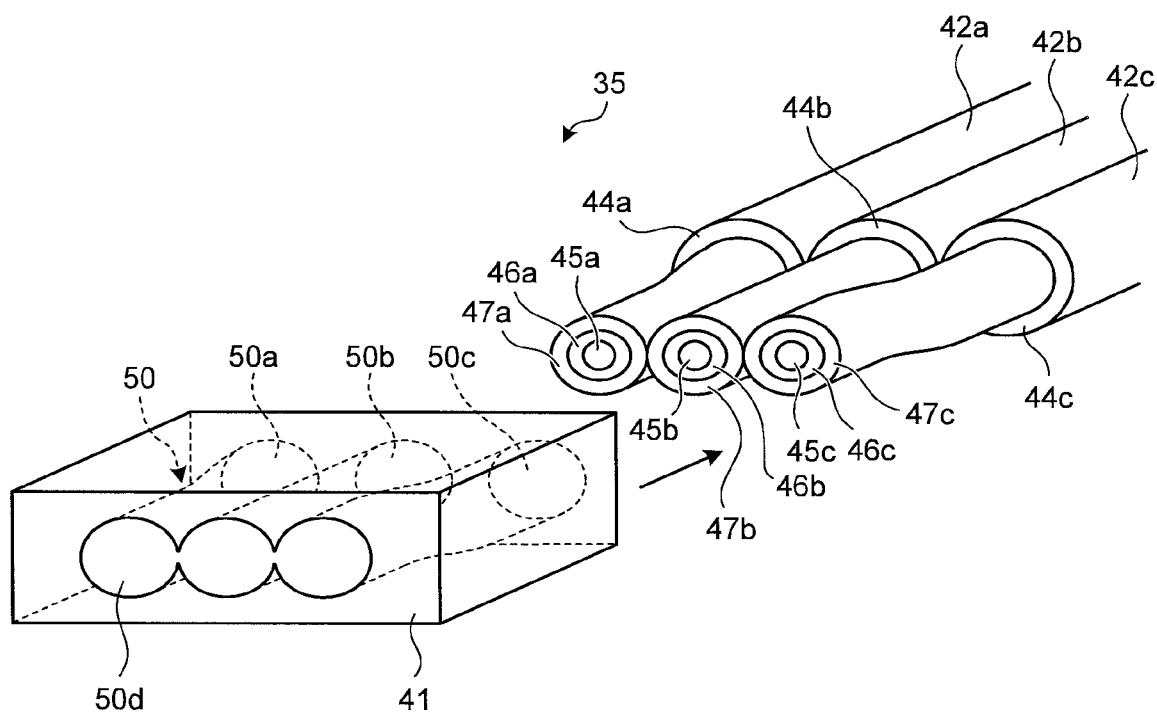
FIG. 3 is a perspective view of the cable assembly and the array block shown in FIG. 2.
Figure 4:
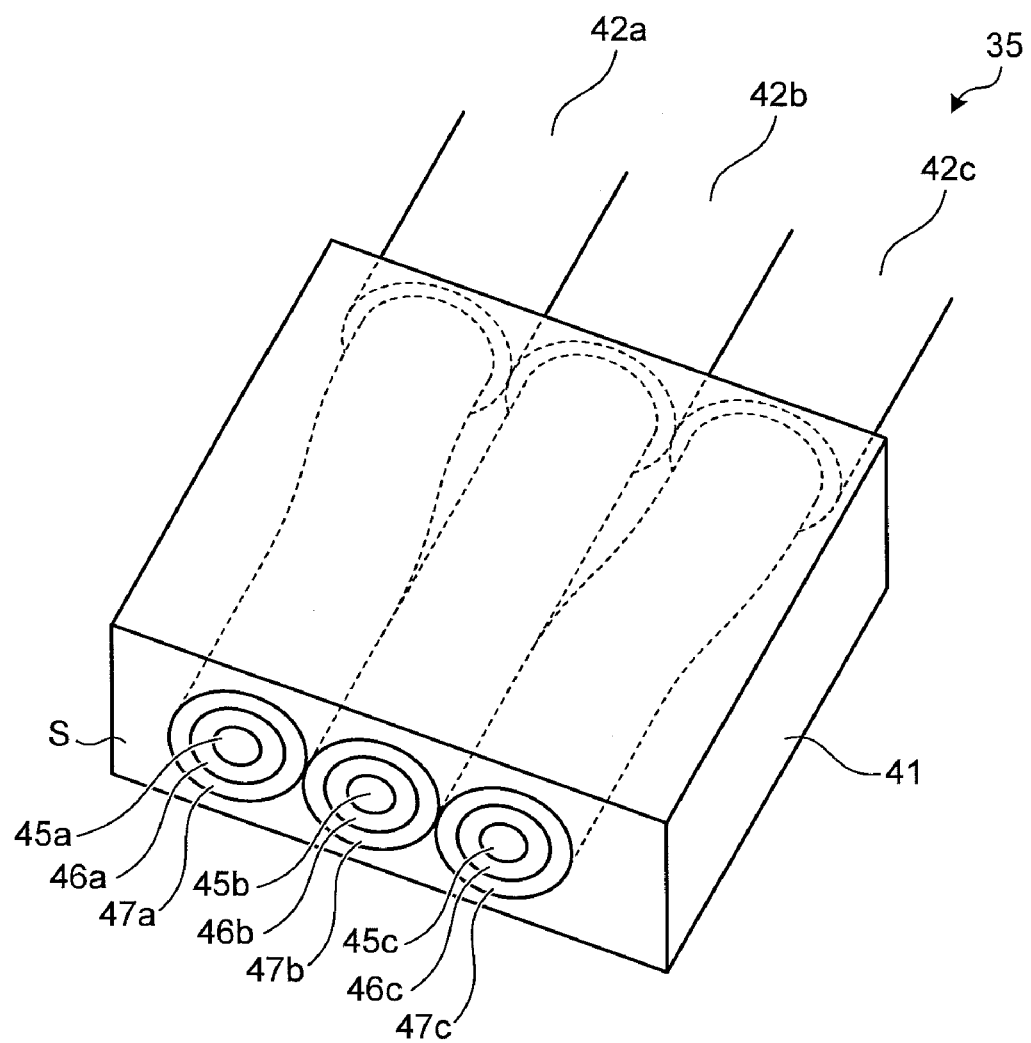
FIG. 4 is a perspective view of the cable assembly to which the array block shown in FIG. 3 is attached at a distal end.
Figure 5:
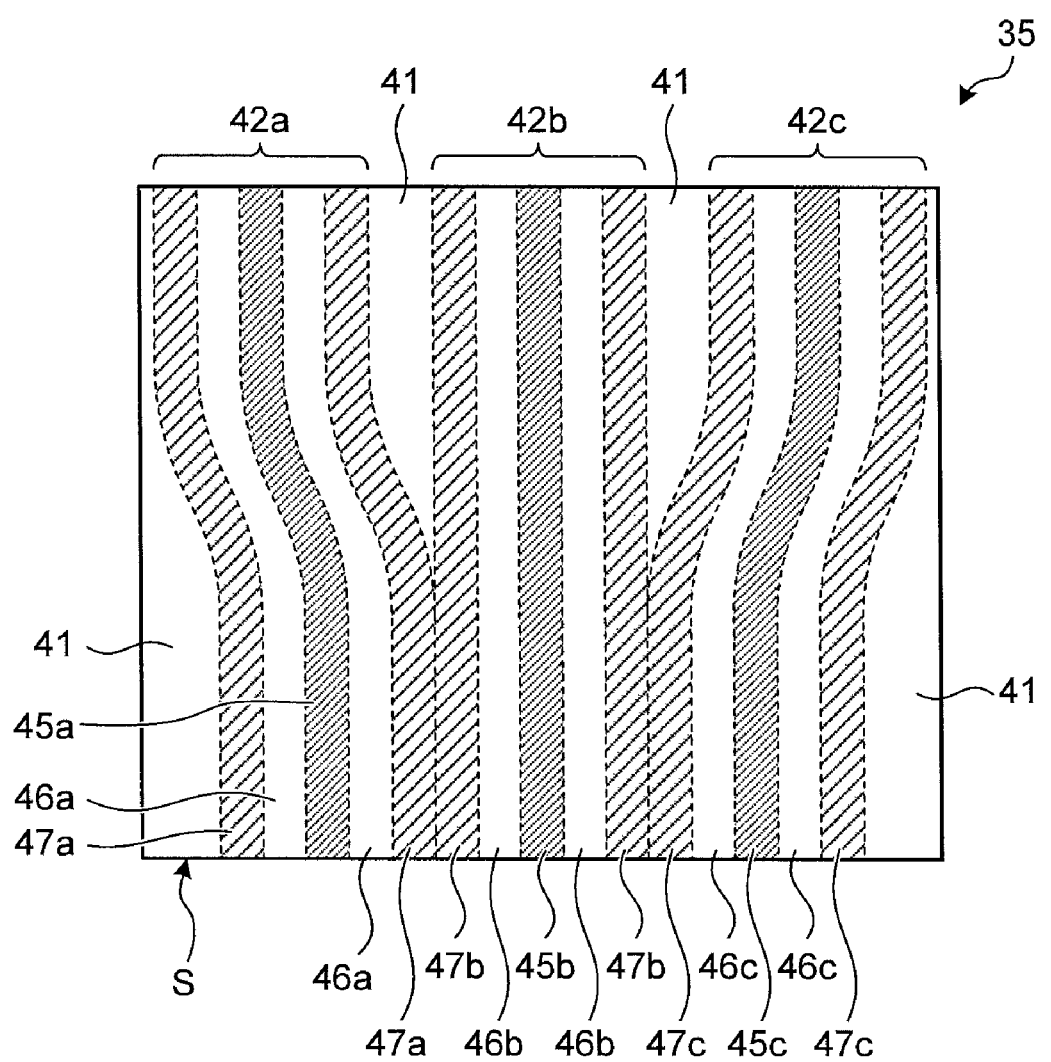
FIG. 5 is a plane view of the cable assembly to which the array block shown in FIG. 3 is attached at the distal end.
Figure 6:
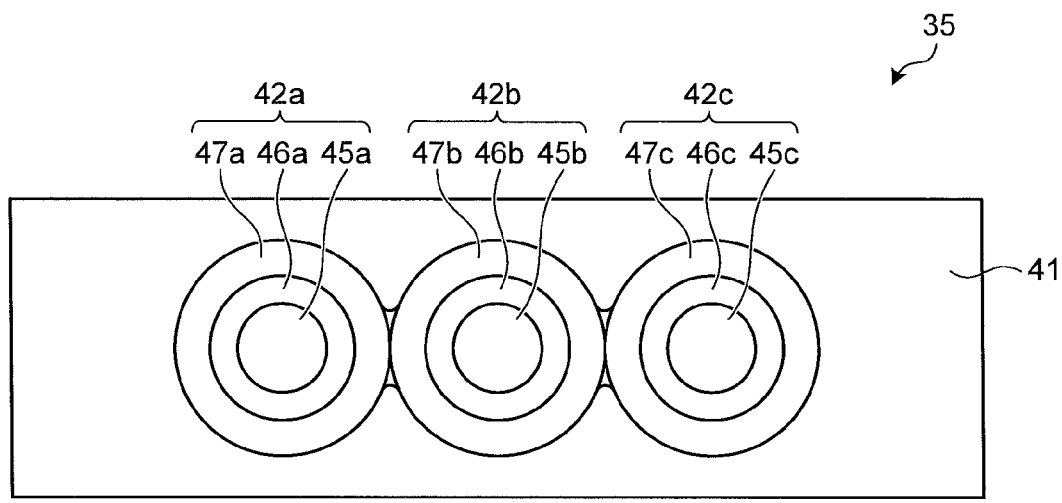
FIG. 6 shows a distal end surface of the cable assembly to which the array block shown in FIG. 3 is attached at the distal end.

Next, the cable assembly 35 will be explained. FIG. 3 is a perspective view of the cable assembly 35 and the array block 41. FIG. 4 is a perspective view of the cable assembly 35 to which the array block 41 is attached at the distal end. FIG. 5 is a plane view of a main part of the cable assembly 35 to which the array block 41 is attached at the distal end. FIG. 6 shows the distal end surface of the cable assembly 35 to which the array block 41 is attached at the distal end. In FIG. 5, constituent members of the signal lines inserted into the inside are shown by a dashed line.

As shown in FIG. 3, the cable assembly 35 is formed by arranging three signal lines 42a to 42c in line, for example. The signal lines 42a to 42c are provided with core wires 45a to 45c that are arranged at a center position and transmit electrical signals, inner insulating bodies 46a to 46c formed in a manner of covering the core wires 45a to 45c, outer conducting bodies 47a to 47c formed in a manner of covering the inner insulating bodies 46a to 46c, and outer insulating bodies 44a to 44c formed in a manner of covering the outer conducting bodies 47a to 47c, respectively. The core wires 45a to 45c are connected to the CCD 31 via the electrode part of the circuit board 34 and transmit a driving signal to the CCD 31. The core wires 45a to 45c transmit an electrical signal corresponding to an image captured by the CCD 31 to the signal processor as an external device. The outer conducting bodies 47a to 47c are connected to an external power supplying device to supply a power voltage to the CCD 31. The outer conducting bodies 47a to 47c are connected to the same power supplying device.

As shown in FIG. 3, the outer insulating bodies 44a to 44c are removed in an area including respective distal edges in the signal lines 42a to 42c and the outer conducting bodies 47a to 47c are formed in a manner of being exposed from the outer insulating bodies 44a to 44c, respectively.

The array block 41 is formed of an insulation material such as a resin. For the purpose of fixing the signal lines 42a to 42c in a state where side surfaces of neighboring outer conducting bodies among the exposed outer conducting bodies 47a to 47c are in contact with each other, the array block 41 includes a fixation hollow 50 which allows fixing the neighboring outer conducting bodies 47a to 47c in the array block 41 while keeping the state where side surfaces are in contact with each other.

The fixation hollow 50 includes, on a surface through which the signal lines 42a to 42c are inserted in the array block 41, insertion openings 50a to 50c respectively for the signal lines 42a to 42c at positions away from each other by a thickness of each of the outer insulating bodies 44a to 44c in the signal lines 42a to 42c. The insertion openings 50a to 50c are formed to have respective inner diameters equivalent to respective diametrical dimensions obtained by joining the core wires 45a to 45c, the inner isolating bodies 46a to 46c, and the outer conducting bodies 47a to 47c, respectively. The insertion openings 50a to 50c are then formed in a manner of linking with each other in the inside of the array block 41 to serve as a single opening 50d at the distal end surface of the array block 41. The lengths of the signal lines 42a to 42c in their extending direction in the array block 41 are almost equivalent to the lengths of the exposed outer conducting bodies 47a to 47c.

The respective exposed areas of the outer conducting bodies 47a to 47c are inserted into the insertion openings 50a to 50c in the array block 41, so that the signal lines 42a to 42c are fixedly arranged in the inside of the array block 41 in such a manner that the side surfaces of the neighboring outer conducting bodies 47a to 47c are in contact as shown in FIGS. 4 and 5. Then, respective edges of the signal lines 42a to 42c fixed in the array block 41 are ground, so that respective edge faces of the core wires 45a to 45c and respective edge faces of the outer conducting bodies 47a to 47c are exposed on the same plane, i.e., a distal end surface S. The signal lines 42a to 42c inserted to the array block 41 in a state of being separated by different insertion openings 50a to 50c are fixedly arranged on the distal end surface S of the array block 41 in a state where the side surfaces of the outer conducting bodies 47a to 47c are in contact in the same opening 50d as shown in FIGS. 4 to 6. Since the outer conducting bodies 47a to 47c are connected to the same power supplying device and have the same function of supplying a power voltage to the CCD 31, the imaging device 20 is able to perform the process of capturing images with no specific problem even while the state where the side surfaces of the outer conducting bodies 47a to 47c are in contact are held.

Figure 7:
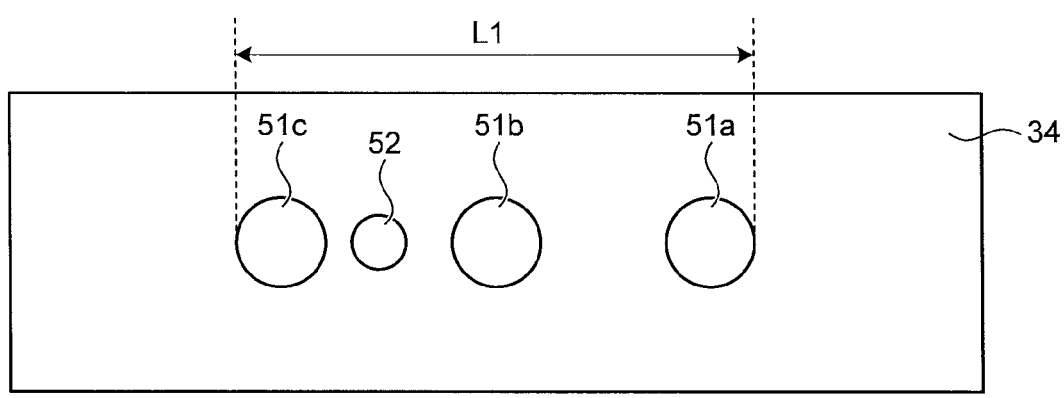
FIG. 7 shows an electrode arrangement on a connection surface of the circuit board shown in FIG. 2 with the cable assembly.

The distal end surface S of the cable assembly 35 to which the array block 41 is attached is connected to the circuit board 34. Next, the circuit board 34 will be explained. FIG. 7 shows an electrode arrangement on a connection surface of the circuit board 34 shown in FIG. 2 with the cable assembly 35, more specifically, on an electrode part formation surface facing the distal end surface S as the surface of the exposed edges in the array block 41.

As shown in FIG. 7, a plurality of core wire electrode parts 51a to 51c are provided on the connection surface of the circuit board 34 with the cable assembly 35 in a protruding manner, the core wire electrode parts 51a to 51c being connected to the edge faces of the core wires 45a to 45c in the signal lines 42a to 42c, respectively. Electrical signals are transmitted between each of the core wires 45a to 45c in the signal lines 42a to 42c and the CCD 31 via the core wire electrode parts 51a to 51c, respectively.

In addition to the core wire electrode parts 51a to 51c, an outer conducting body electrode part 52 which is connected to a part of the edge faces of the plurality of outer conducting bodies 47a to 47c in the cable assembly 35 is provided on the circuit board 34 in a protruding manner. The outer conducting bodies 47a to 47c are connected to the same power supplying device and have the same function of supplying a power voltage to the CCD 31. Moreover, since the outer conducting bodies 47a to 47c are fixed in the state where side surfaces are in contact by the array block 41, the outer conducting bodies 47a to 47c are fixedly arranged in a state of having electrical continuity. Therefore, the circuit board 34 only provided with one outer conducting body electrode part 52 to be connected to a part of the edge faces of the outer conducting bodies 47a to 47c enables all the outer conducting bodies 47a to 47c to be electrically connected to the CCD 31 without providing a plurality of outer conducting body electrode parts to be connected to the outer conducting bodies 47a to 47c. Thus, the power voltage to be supplied from the outer conducting bodies 47a to 47c can be supplied to the CCD 31 only via the one outer conducting body electrode part 52. Since it is sufficient that the outer conducting body electrode part 52 is connected to at least a part of the edge faces of the outer conducting bodies 47a to 47c whose side surfaces are mutually in contact, there is no necessity of increasing an area of the outer conducting body electrode part 52 in accordance with a radial thickness of the outer conducting bodies 47a to 47c.

In the circuit board 34, the outer conducting body electrode part 52 is formed to locate at an inner side from the core wire electrode parts 51a and 51c locating outermost among the plurality of core wire electrode parts 51a to 51c on the electrode part formation surface.

Figure 8:
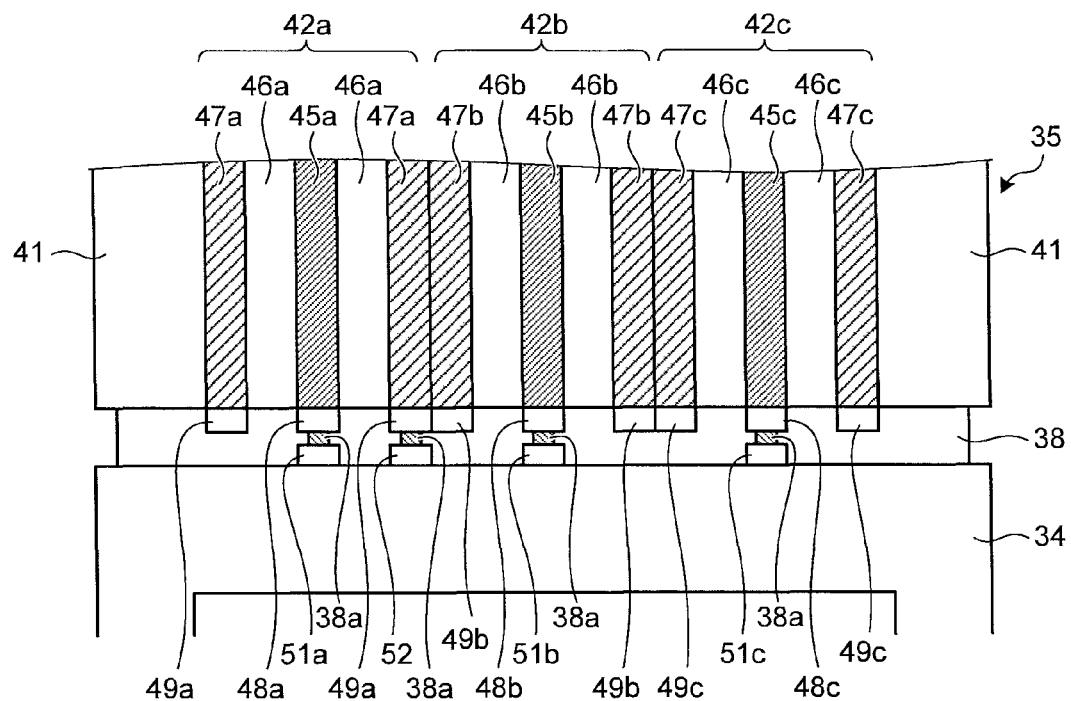
FIG. 8 is a cross sectional view showing a case where the circuit board and the cable assembly shown in FIG. 2 are connected.

FIG. 8 is a cross sectional view showing a case where the circuit board 34 and the cable assembly 35 are connected and showing a case of the cross section cut along a plane which is parallel to the extending direction of the signal lines 42a to 42c and goes through respective centers of the core wires 45a to 45c. In FIG. 8, an illustration of the IC and the capacitor on the connection surface with the CCD 31 is omitted.

As shown in FIG. 8, core wire conductive layers 48a to 48c are formed on front edge faces of the core wires 45a to 45c exposed from the distal end surface S of the array block 41, respectively. Besides, outer conducting body conductive layers 49a to 49c are formed on front edge faces of the outer conducting bodies 47a to 47c exposed from the distal end surface S of the array block 41, respectively. The core wire conductive layers 48a to 48c and the outer conducting body conductive layers 49a to 49c are formed by a metal film by using a plating process or a sputtering process. The core wire conductive layers 48a to 48c and the outer conducting body conductive layers 49a to 49c may have a single layer structure or a multilayer structure. For example, in a case of layering a gold (Au) film and a nickel (Ni) film on each of the front edge faces so that the nickel (Ni) film comes to a front surface side, it is possible to realize a strong connection with an external connection end surface and further to perform either a solder bumping process or a gold (Au) bumping process, and thereby to enhance the flexibility in an aspect of bonding.

The circuit board 34 is connected to the cable assembly 35 after positioning is performed in a state where the electrode part formation surface on which the core wire electrode parts 51a to 51c and the outer conducting body electrode part 52 are formed faces the distal end surface S which is the surface on which the edge faces of the outer conducting bodies 47a to 47c and the core wires 45a to 45c fixed by the array block 41 are exposed. By compressively bonding the electrode part formation surface of the circuit board 34 and the distal end surface of the array block 41 of the cable assembly 35 in a state where the ACF 38 is provided to intervene in between, respective edge faces of the core wires 45a to 45c and the core wire electrode parts 51a to 51c are collectively and electrically connected respectively and a part of the edge faces of the outer conducting bodies 47a to 47c and the outer conducting body electrode part 52 are collectively and electrically connected as shown in FIG. 8. The respective edge faces of the core wires 45a to 45c and the core wire electrode parts 51a to 51c, and the part of the edge faces of the outer conducting bodies 47a to 47c and the outer conducting body electrode part 52 are electrically connected via respective conductive materials 38a included in the ACF 38 at predetermined intervals. The circuit board 34 and the cable assembly 35 are bonded via a thermal compression bonding, for example.

As described, since the cable assembly 35 and the circuit board 34 are connected in the state where side surfaces of neighboring outer conducting bodies among the outer conducting bodies 47a to 47c of the signal lines 42a to 42c are in contact, it is possible in the embodiment to electrically connect all the outer conducting bodies 47a to 47c and the CCD 31 only by providing one outer conducting body electrode part 52 corresponding to a part of the edge faces of the plurality of outer conducting bodies 47a to 47c on the circuit board 34.

Figure 9:
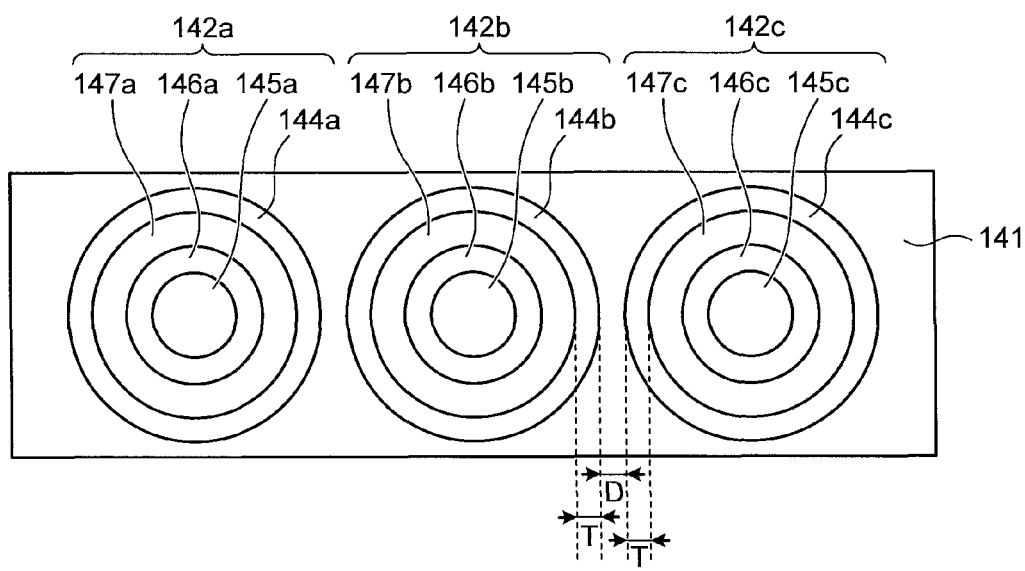
FIG. 9 shows a distal end surface of a conventional cable assembly.
Figure 10:
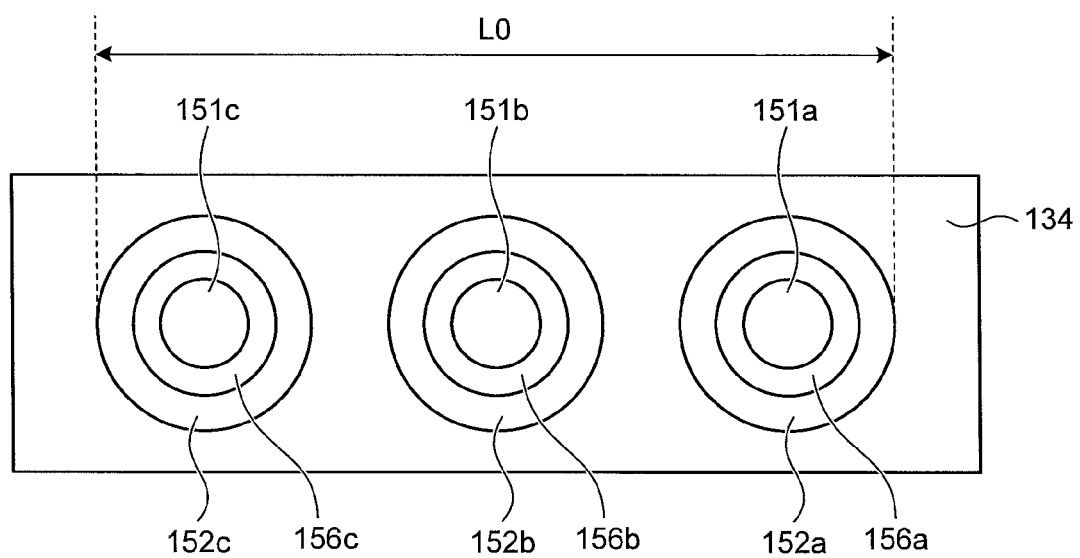
FIG. 10 shows an electrode arrangement on a connection surface of a conventional circuit board with the cable assembly.

Here, a connection of a conventional cable assembly and a circuit board will be explained. FIG. 9 shows a distal end surface of a conventional cable assembly. FIG. 10 shows an electrode arrangement on a connection surface of a conventional circuit board with a cable assembly. As shown in FIG. 9, signal lines 142a to 142c are inserted to respective fixation holes of an array block 141 one by one in a separated state and a distal end part of the cable assembly is fixed conventionally, the signal lines 142a to 142c being formed by core wires 145a to 145c, inner insulating bodies 146a to 146c, outer conducting bodies 147a to 147c, and outer insulating bodies 144a to 144c having a radial thickness T. Therefore, the signal lines 142a to 142c are fixed in a state of being separated with each other on a distal end surface of the array block 141. With this configuration, a plurality of outer conducting body electrode parts 152a to 152c respectively for the outer conducting bodies 147a to 147c are formed in a manner of surrounding core wire electrode parts 151a to 151c via inner insulating bodies 156a to 156c so as to be connected to all of the outer conducting bodies 147a to 147c fixed in the separated state, in addition to a plurality of core wire electrode parts 151a to 151c respectively for the core wires 142a to 142c on a connection surface of a circuit board 134 with the cable assembly. Then, since the outer conducting body electrode parts 152a to 152c are formed at positions respectively corresponding to the outer conducting bodies 147a to 147c, the outer conducting body electrode parts 152a to 152c are formed at positions away from each other by (2T+D) when each thickness of the outer insulating bodies 144a to 144c is denoted by a letter "T" and each distance between neighboring signal lines among the signal lines 142a to 142c is denoted by a letter "D".

As described in the conventional circuit board, it is necessary to provide the plurality of outer conducting body electrode parts 152a to 152c, to respectively deal with the outer conducting bodies 147a to 147c of the signal lines 142a to 142c fixedly arranged in the separated state, at positions away from each other respectively in accordance with the outer conducting bodies 147a to 147c and in sizes respectively in accordance with the shapes of the outer conducting bodies 147a to 147c. Thus, since it is necessary to secure a certain area having a width "L0" shown in FIG. 10, for example, for the plurality of outer conducting body electrode parts provided in accordance with the positions of the arranged outer conducting bodies 147a to 147c in the conventional circuit board, there is a limitation on the downsizing of the circuit board and also a limitation of making the outer diameter at the distal end part of the insertion unit small due to the failure in the downsizing of the imaging element package.

In contrast to this, respective distal edge parts of the outer conducting bodies 47a to 47c of the signal lines 42a to 42c are exposed and the cable assembly 35 and the circuit board 34 are connected in the state where side surfaces of neighboring outer conducting bodies among the exposed outer conducting bodies 47a to 47c are in contact in the embodiment. Specifically, the outer conducting bodies 47a to 47c are fixed in the state where side surfaces of neighboring outer conducting bodies are in contact without the intervention of the outer insulating bodies 44a to 44c and kept in the state of having electrical continuity. Therefore, the circuit board 34 only provided with, as an outer conducting body electrode part for the plurality of outer conducting bodies 47a to 47c, one outer conducting body electrode part 52 to be connected to a part of the edge faces of the plurality of outer conducting bodies 47a to 47c enables all the outer conducting bodies 47a to 47c to be electrically connected to the CCD 31. In other words, it is not necessary to provide a plurality of outer conducting body electrode parts for respective outer conducting bodies, which results in no necessity of separating the outer conducting bodies. Therefore in the embodiment, it is possible to make a length "L1" of an area for the arranged outer conducting body electrode part and the core wire electrode parts shorter than the length "L0" in the conventional technique by the distance between signal lines as well as the respective thicknesses of the outer insulating bodies 44a to 44c, and moreover to make the number of outer conducting body electrode parts only one, compared to the conventional technique in which the plurality of outer conducting body electrode parts are provided away from each other to deal with the respective outer conducting bodies fixed separately from each other. As a result of this, it is possible to make the area required for the electrode parts in the circuit board 34 significantly small and realize the downsizing of the circuit board 34 in the embodiment compared to the conventional technique.

Since the outer conducting body electrode parts 152a to 152c are formed as far as the area at the outer side from the core wire electrode parts 151a to 151c in a manner of surrounding the core wire electrode parts 151a to 151c in the conventional circuit board, it is necessary to widely secure the area for the electrode parts across the area at the outer sides from the core wire electrode parts 151a to 151c. In contrast to this, the outer conducting body electrode part 52 is formed to locate at an inner side from the core wire electrode part 51a locating outermost among the plurality of core wire electrode parts 51a to 51c on the electrode part formation surface in the circuit board 34 according to the embodiment. Since it is only necessary to secure, as the area for the electrode part, an area whose limit is defined by the core wire electrode parts 51a to 51c in the embodiment, it is possible to make the area to be secured for the electrode part small compared to the conventional technique and realize the downsizing of the circuit board 34. As a result of this, it is possible to downsize the circuit board 34, thereby to downsize the imaging element package, and further to make the outer diameter at the distal end part of the insertion unit small according to the embodiment.

Figure 11:
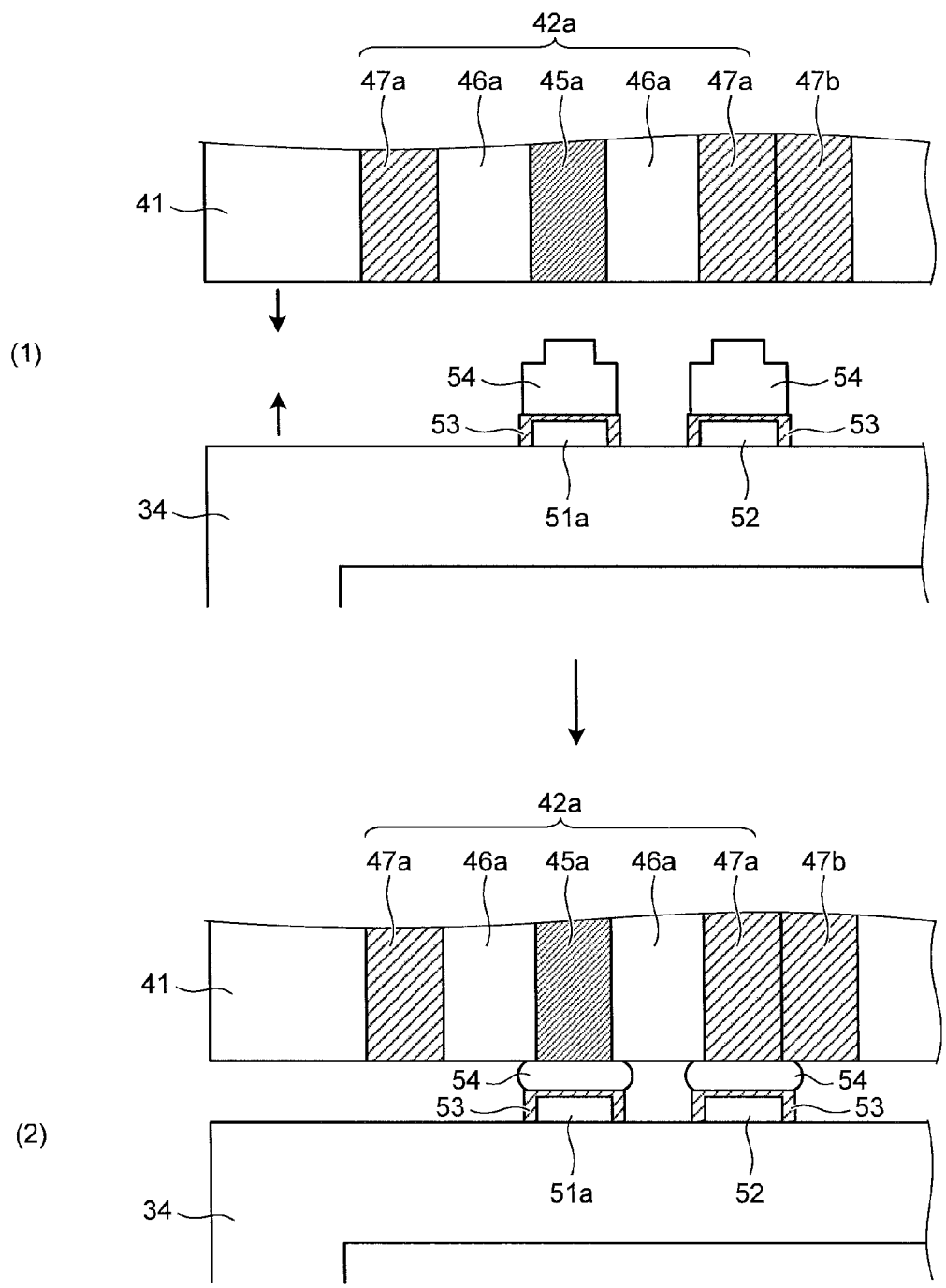
FIG. 11 is a cross sectional view for explaining another example of a method of connecting the circuit board and the cable assembly shown in FIG. 2.

While the example of using the ACF 38 for bonding the circuit board 34 and the cable assembly 35 to which the array block 41 is attached at the distal end is taken as an example and explained in the embodiment, the present invention is not, of course, limited thereto and anisotropic conductive adhesive paste (ACP) may be used. As shown at (1) in FIG. 11, respective protruding electrodes 54 may be formed on the core wire electrode parts 51a to 51c and on the outer conducting body electrode part 52, and the core wires 45a to 45c and the core wire electrode parts 51a to 51c and the outer conducting body 47a and the outer conducting body electrode part 52 may be bonded via the respective protruding electrodes 54 having crushed as shown at (2) in FIG. 11 when the circuit board 34 and the cable assembly 35 are compressively bonded. The protruding electrodes 54 are formed on the core wire electrode parts 51a to 51c and on the outer conducting body electrode part 52 after giving a gold plating 53 thereon. In the case of using the protruding electrodes 54, the circuit board 34 and the cable assembly 35 are surely connected in a state of covering a tolerance in width between the distal end surface S and the circuit board 34 by the crush of the protruding electrodes 54 in the compressive bonding even when the distal end surface S of the array block 41 and the electrode part formation surface of the circuit board 34 are not completely parallel at the time of the grinding of the signal lines 42a to 42c fixed by the array block 41.

Figure 12:
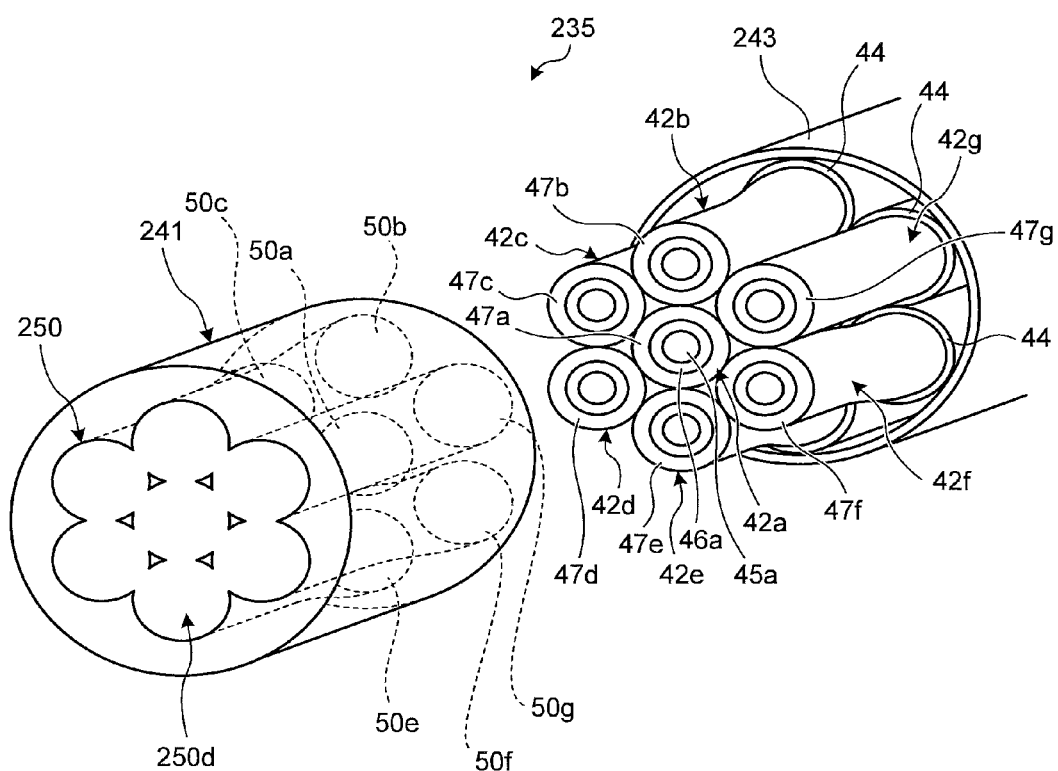
FIG. 12 is a perspective view of another example between the cable assembly and the array block shown in FIG. 2.

Besides, while the case of arranging the signal lines 42a to 42c in line by the array block 41 is taken as an example and explained as the embodiment, the present invention is not limited thereto and may have applicability to a cable assembly 235 bundled by an outer shield 243 like signal lines 42a to 42g shown in FIG. 12.

Similarly in this case, respective outer insulating bodies 44 are removed in the area including respective distal edges in the signal lines 42a to 42g and outer conducting bodies 47a to 47g are formed in a manner of being exposed from the respective outer insulating bodies 44 as shown in FIG. 12. In this case, a fixation hollow 250 is provided in an array block 241 to allow fixation in the array block 241 while keeping a state where side surfaces of neighboring outer conducting bodies among the exposed outer conducting bodies 47a to 47g are in contact with each other. The fixation hollow 250 includes, on an insertion surface of the signal lines 42a to 42g, insertion openings 50a to 50g formed respectively for the signal lines 42a to 42g in a manner of linking with each other in the inside of the array block 241 to serve as a single opening 250d on the distal end surface of the array block 241. Therefore, the signal lines 42a to 42g which are inserted into the array block 241 in a state of being separated from each other via respectively different insertion openings 50a to 50g are fixedly arranged on the distal end surface of the array block 241 in the state where side surfaces of the outer conducting bodies 47a to 47g are in contact in the opening 250d as shown in FIG. 13.

Figure 14:
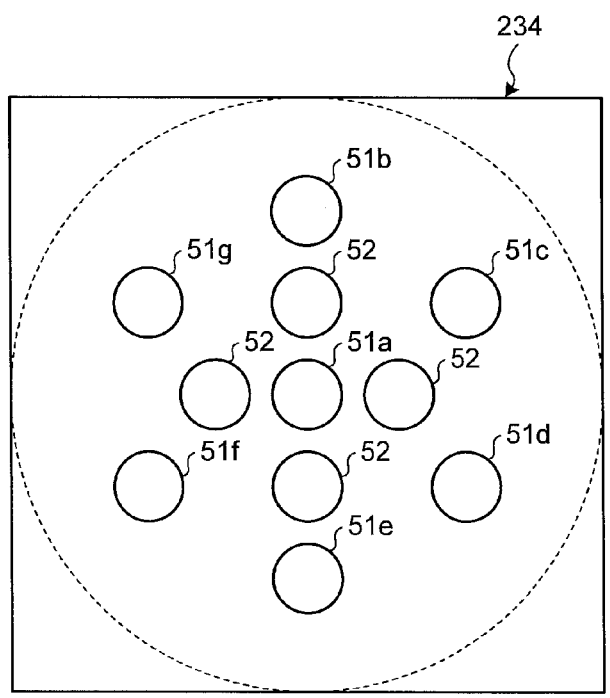
FIG. 14 shows an electrode arrangement in a circuit board connected to the cable assembly shown in FIG. 13.
Figure 15:
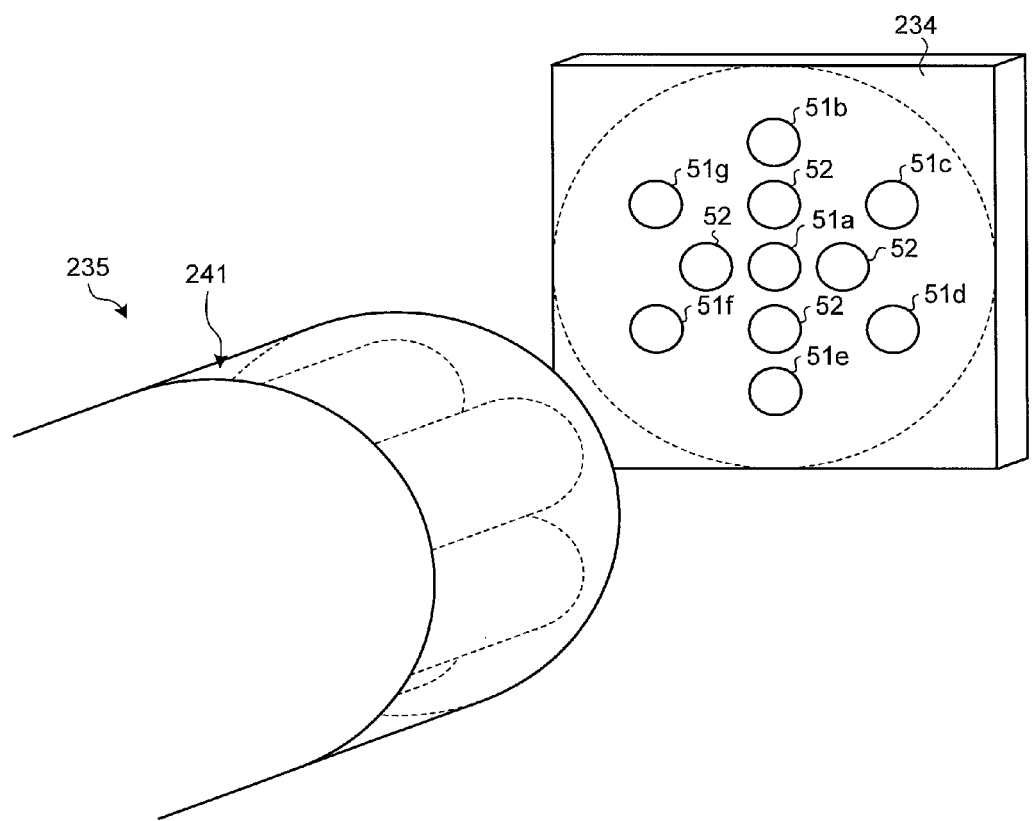
FIG. 15 is a perspective view for explaining a connection between the cable assembly shown in FIG. 13 and the circuit board shown in FIG. 14.

As shown in FIG. 14, a circuit board 234 to be connected to the distal end surface of the array block 241 is provided with a plurality of core wire electrode parts 51a to 51g which are connected to the respective edge faces of the core wires 45a to 45g in the signal lines 42a to 42g, respectively on the connection surface with the cable assembly 235. In addition to the core wire electrode parts 51a to 51g, the circuit board 234 is provided with a plurality of outer conducting body electrode parts 52 to be connected to a part of the edge faces of the plurality of outer conducting bodies 47a to 47g in the cable assembly 235. After the core wires and the outer conducting bodies 47a to 47g fixed in the array block 241 are ground, the circuit board 234 is, after positioning is performed, connected to the cable assembly 235 via the ACF 38 in a state where the electrode part formation surface on which the core wire electrode parts 51a to 51g and the outer conducting body electrode parts 52 are formed faces the distal end surface which is the surface on which the edge faces of the outer conducting bodies 47a to 47g and the core wires fixed by the array block 241 are exposed as shown in FIG. 15.

Figure 16:
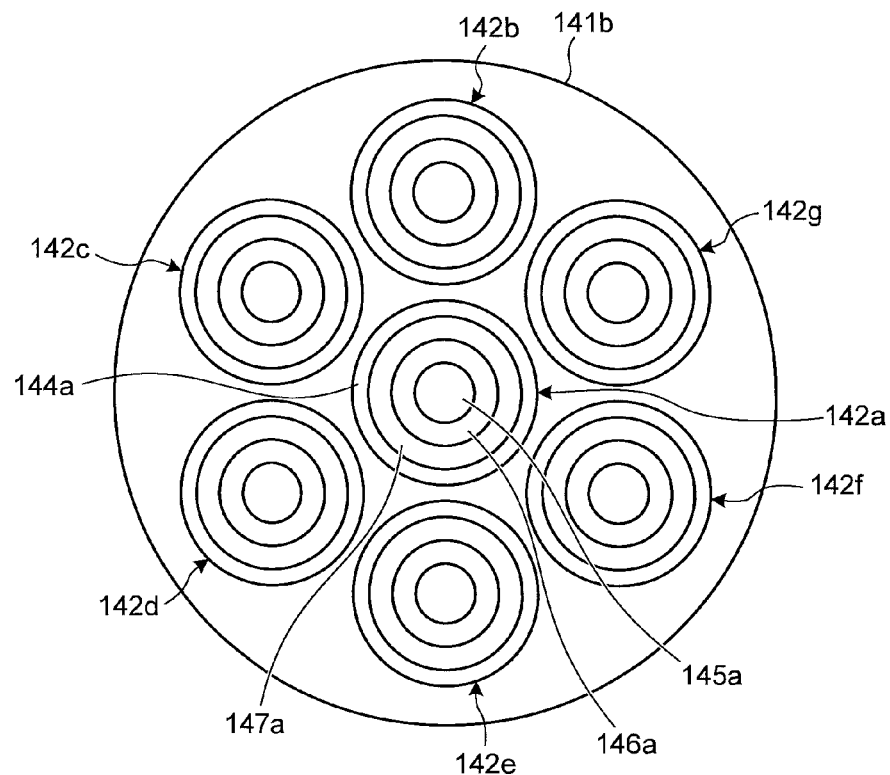
FIG. 16 shows another example of a distal end surface of the conventional cable assembly.
Figure 17:
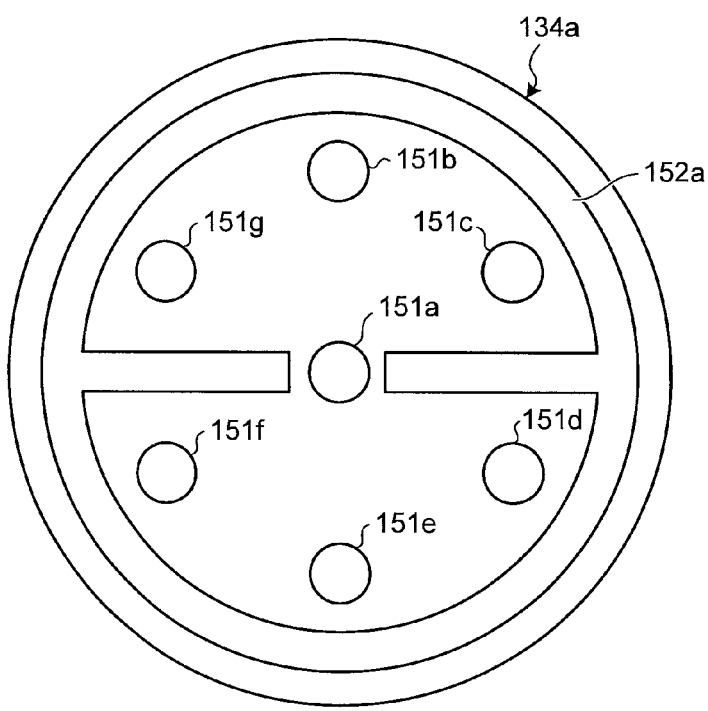
FIG. 17 shows another example of an electrode arrangement on a connection surface of the conventional circuit board with the cable assembly.

Here, since signal lines 142a to 142g are inserted to respective fixation holes of an array block 141b in a separated state as shown in FIG. 16 in the conventional technique, the signal lines 142a to 142g are fixed in a state of being separated with each other on a distal end surface of the array block 141b. With this configuration, an outer conducting body electrode part 152a is formed in a manner of surrounding an outer side of the core wire electrode parts 151b to 151g so as to be connected to all of the outer conducting bodies 147a to 147g fixed in the separated state in addition to a plurality of core wire electrode parts 151a to 151g respectively for the core wires 142a to 142g on a connection surface of a circuit board 134a with the cable assembly, and therefore it is necessary to secure an area for the electrode part to fit with the outer conducting body electrode part 152a as shown in FIG. 17.

Figure 13:
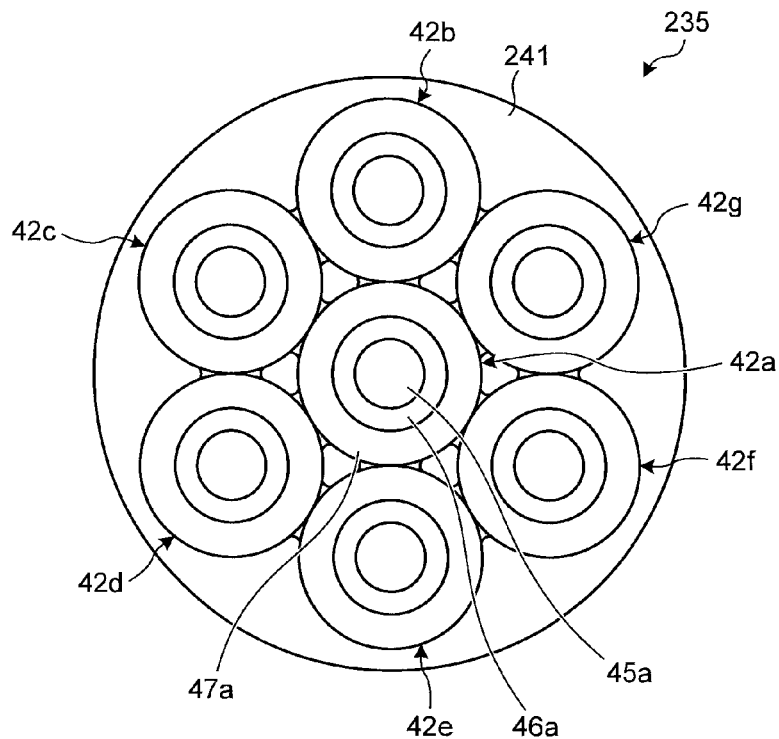
FIG. 13 is a plane view of a cable assembly to which the array block shown in FIG. 12 is attached at a distal end.

In contrast to this, since the outer conducting bodies 47a to 47g are fixed in the state where side surfaces are in contact without the intervention of the outer insulating body 44 in the case shown in FIG. 13, it is possible in the circuit board 234 shown in FIG. 14 to electrically connect all the outer conducting bodies 47a to 47g and the CCD 31 only by providing several outer conducting body electrode parts 52 which can be connected to a part of the edge faces of the outer conducting bodies 47a to 47g, without providing the outer conducting body electrode parts the number of which is equivalent to that of the outer conducting bodies 47a to 47g.

In the circuit board 234, since it is only necessary to secure, as the area for the electrode part, an area whose limit is defined by the core wire electrode parts 51b to 51g by forming respective outer conducting body electrode parts 52 to locate at an inner side from the core wire electrode parts 51b and 51g locating outermost among the plurality of core wire electrode parts 51a to 51g, it is possible to realize the downsizing of the circuit board 234.

Moreover, since a pressure to be imposed on the signal lines 42a to 42g from a side of the circuit board 234 in connection can be evenly dispersed by forming the plurality of outer conducting body electrode parts 52 at regular intervals in a manner of centering around the core wire electrode part 51a locating at the center as shown in the circuit board 234 in FIG. 14, it is possible to stabilize an attachment angle of the cable assembly 235 with respect to the circuit board 234 in any area on the circuit board 234.

While the case of being used for a medical endoscope is taken as an example and explained in the embodiment, the present invention is not, of course, limited thereto and may have applicability to a cable used for optical transmission, for example.

Besides, while the cable assembly is manufactured by preparing the array block provided with a fixation hole in advance prior to the manufacturing of the cable assembly, inserting a plurality of signal lines from its insertion opening, and fixing the signal lines to the array block in the embodiment, the present invention is not limited thereto, and an array block may be formed by arranging respective signal lines in the state as shown in FIG. 4, for example and then solidifying an area including the distal edges by a resin to manufacture the cable assembly.

In a cable assembly provided with a plurality of signal lines each of which is formed by a core wire, an inner insulating body, an outer conducting body, and an outer insulating body according to the present invention, since respective signal lines are formed in a manner of exposing respective outer conducting bodies from respective insulating bodies in an area at least including respective distal edges and a fixation member fixes the signal lines in a state where side surfaces of neighboring outer conducting bodies among the exposed outer conducting bodies are in contact, it is only necessary to form, as an outer conducting body electrode part in addition to a plurality of core wire electrode parts, an electrode part which is connected to a part of edge faces of the plurality of outer conducting bodies on the substrate to be connected to the cable assembly, and thereby downsizing of the substrate can be achieved without a necessity of securing a wide area for the electrode part.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A mounting assembly provided with: a cable assembly including a plurality of signal lines each of which is formed by a core wire, an inner insulating body which covers the core wire, an outer conducting body which covers the inner insulating body, and an outer insulating body which covers the outer conducting body; and a substrate to be connected to the cable assembly, wherein
the cable assembly includes a fixation member that fixes the plurality of signal lines in a predetermined array state, wherein
the signal lines are formed in a manner of exposing respective outer conducting bodies from respective outer insulating bodies in an area at least including respective distal edges,
the fixation member fixes the signal lines in a state where side surfaces of neighboring outer conducting bodies among the exposed outer conducting bodies are in contact and in a manner of exposing respective edge faces of the plurality of outer conducting bodies and respective edge faces of the plurality of core wires, and
the substrate includes an electrode part formation surface which is a surface on which a plurality of core wire electrode parts and an outer conducting body electrode part are formed and faces an edge face exposure surface of the fixation member, the plurality of core wire electrode parts being connected to the respective edge faces of the core wires in the plurality of signal lines and the outer conducting body electrode part being connected to a part of the edge faces of the plurality of outer conducting bodies fixed in the state where the side surfaces are in contact.

2. The mounting assembly according to claim 1, wherein
the fixation member fixes the signal lines in a manner of exposing, on a same plane, the edge faces of the plurality of outer conducting bodies and the edge faces of the plurality of core wires fixed in the state where the side surfaces are in contact, and
the substrate is connected to the cable assembly in a state where the electrode part formation surface faces the edge face exposure surface of the fixation member, so that the respective edge faces of the core wires in the cable assembly and the respective core wire electrode parts are connected and the part of the edge faces of the outer conducting bodies and the outer conducting body electrode part are connected.

3. The mounting assembly according to claim 1, wherein the outer conducting body electrode part is formed to locate at an inner side from a core wire electrode part locating outermost among the plurality of core wire electrode parts on the electrode part formation surface in the substrate.

4. The mounting assembly according to claim 1, wherein the substrate is electrically connected to an imaging element.

5. A cable assembly including a plurality of signal lines each of which is formed by a core wire, an inner insulating body which covers the core wire, an outer conducting body which covers the inner insulating body, and an outer insulating body which covers the outer conducting body, comprising
a fixation member that fixes the plurality of signal lines in a predetermined array state, wherein
the signal lines are formed in a manner of exposing respective outer conducting bodies from respective outer insulating bodies in an area at least including respective distal edges, and the fixation member fixes the signal lines in a state where side surfaces of neighboring outer conducting bodies among the exposed outer conducting bodies are in contact.

6. The cable assembly according to claim 5, wherein the fixation member fixes the signal lines in a manner of exposing, on a same plane, edge faces of the outer conducting bodies and edge faces of the core wires.

* * * * *